United States Patent
Seo

(10) Patent No.: US 10,759,839 B2
(45) Date of Patent: Sep. 1, 2020

(54) CELL-PENETRATING PEPTIDE

(71) Applicant: NEOREGEN BIOTECH, Gyeonggi-do (KR)

(72) Inventor: Jeong Min Seo, Seoul (KR)

(73) Assignee: NEOREGEN BIOTECH, Gyeonggi-Do (KR)

( * ) Notice: Subject to any disclaimer, the term of this patent is extended or adjusted under 35 U.S.C. 154(b) by 4 days.

(21) Appl. No.: 16/092,276

(22) PCT Filed: Apr. 7, 2017

(86) PCT No.: PCT/KR2017/003803
§ 371 (c)(1),
(2) Date: Oct. 9, 2018

(87) PCT Pub. No.: WO2017/176081
PCT Pub. Date: Oct. 12, 2017

(65) Prior Publication Data
US 2019/0127431 A1   May 2, 2019

(30) Foreign Application Priority Data

Apr. 7, 2016   (KR) .................. 10-2016-0042730
Aug. 25, 2016  (KR) .................. 10-2016-0108409

(51) Int. Cl.
| | | |
|---|---|---|
| *A61K 38/00* | (2006.01) | |
| *C07K 14/47* | (2006.01) | |
| *A61K 38/16* | (2006.01) | |
| *A61K 38/17* | (2006.01) | |
| *C07K 14/415* | (2006.01) | |
| *A23L 33/18* | (2016.01) | |
| *C07K 14/00* | (2006.01) | |

(52) U.S. Cl.
CPC .......... *C07K 14/4746* (2013.01); *A23L 33/18* (2016.08); *A61K 38/00* (2013.01); *A61K 38/1758* (2013.01); *C07K 14/001* (2013.01); *C07K 14/415* (2013.01); *C07K 2319/01* (2013.01)

(58) Field of Classification Search
CPC .................. A23L 33/18; A61K 38/00
See application file for complete search history.

(56) References Cited

FOREIGN PATENT DOCUMENTS

| KR | 10-2016-0028754 A | 3/2016 |
|---|---|---|
| WO | 2009/021468 A1 | 2/2009 |
| WO | WO 2014/041505 A1 | 3/2014 |
| WO | WO 2014/205518 A1 | 12/2014 |
| WO | WO 2015/075747 A1 | 5/2015 |

OTHER PUBLICATIONS

Elmquist et al., Experimental Cell Research 269, 237-244 (2001) (Year: 2001).*
Jarver and Langel, DDT vol. 9, No. 9 May 2004 (Year: 2004).*
GenBank IDXP 002873637, [retrieved from internet Nov. 29, 2019 from https://www.ncbi.nlm.nih.gov/protein/XP_002873637]. (Year: 2017).*
Human Molecular Genetics, 2004, vol. 13, No. 1 69-78 (Year: 2004).*
Molecular Genetics and Metabolism 72, 254-259 (2001 (Year: 2001).*
European Search Report for EP17779381.7 dated Mar. 1, 2019 from European patent office in a counterpart European patent application.
Keiji Numata et al., "Library screening of cell-penetrating peptide for BY-2 cells, leaves of *Arabidopsis*, tobacco, tomato, poplar, and rice callus", Scientific Reports, vol. 8, No. 1, 2018.
Dana Maria Copolovici et al., "Cell-Penetrating Peptides: Design, Synthesis, and Applications", ACS NANO, vol. 8, No. 3, pp. 1972-1994, 2014.
Unknown, "UniProtKB-D7M5X9 (D7M5X9_ARALL)", Retrieved from the Internet: URL:https://www.uniprot.org/uniprot/D7M5X9, 2010.
International Search Report for PCT/KR20171003803 dated Jul. 10, 2017.
Chuah et al., "Gene introduction into the Mitochondria of *Arabidopsis thaliana* via Peptide-based Carriers", Scientific Reports, vol. 5, No. 7751, pp. 1-7, 2015.
NCBI, GenPept accession No. XP_002873637.1, (Jun. 11, 2010 ).
Takashi Sera, "Zinc-finger-based artificial transcription factors and their applications", Advanced Drug Delivery Review, vol. 61, pp. 513-526, 2009 (Abstract is submitted herewith).
Office action dated Feb. 17, 2017 from Korean Patent Office in a counterpart Korean Patent Application No. 10-2016-0108409 (all the cited references are listed in this IDS.) (English translation is submitted herewith).

* cited by examiner

*Primary Examiner* — Juliet C Switzer
*Assistant Examiner* — Joseph Fischer
(74) *Attorney, Agent, or Firm* — The PL Law Group, PLLC

(57) ABSTRACT

A cell-penetrating peptide has remarkably excellent cell penetration efficiency, and is capable of penetrating 100% into all cells within 1 hour even in an environment including serum or sera, as well as a stable structure. Therefore, it is possible to move a cargo into the cell while maintaining the function of the cargo without damaging the same.

16 Claims, 8 Drawing Sheets

Specification includes a Sequence Listing.

CONFOCAL IMAGE

GREEN: Ara-27-FITC
RED: membrane marker
BLUE: DAPI

ANTI-CANCER EFFECT ON BONE MARROW CANCER CELL LINE

OVER EXPRESSD ICT-53 IN E. COLI BL21

CELL-PENETRATING PEPTIDE

CROSS REFERENCE TO RELATED APPLICATIONS AND CLAIM OF PRIORITY

This application claims benefit under 35 U.S.C. 119(e), 120, 121, or 365(c), and is a National Stage entry from International Application No. PCT/KR2017/003803, filed Apr. 7, 2017 which claims priority to the benefit of Korean Patent Application No. 10-2016-0042730 filed on Apr. 7, 2016 and 10-2016-0108409 filed on Aug. 25, 2016 in the Korean Intellectual Property Office, the entire contents of which are incorporated herein by reference.

TECHNICAL FIELD

The present invention relates to a cell-penetrating peptide found in a plant-derived protein.

BACKGROUND ART

A cell-penetrating peptide (CPP), which is a peptide having a property capable of penetrating a cell membrane, usually includes 30 amino acids or less, and is known to have a property of freely passing through a lipid bilayer membrane. The CPP is also referred to as protein-transduction domains (PTDs) and membrane-translocating sequences (MTSs), and may pass through the cell membrane in a form of being coupled to an object to be delivered or being mixed therewith, thus to transport the object to be delivered such as a protein, DNA, RNA, or the like into a cell, as well as into cytoplasm, an intracellular organelle, or a nucleus.

The cell membrane of higher animals consists of a phospholipid bilayer. Due to the lipid bilayers being hydrophobic, it is almost impossible for most of the peptides, proteins, nucleotides, liposomes, and the like to migrate into the cell. Accordingly, the cell membrane may act as an obstacle in the process of migrating the peptides, proteins, a drug formulation of compound, or a gene therapy agent into the cell. To overcome this problem, migration methods using a cationic lipid, polyethyleneimine (PEI), a viral vector, or electroporation have been widely used in the art.

However, these methods have a limit to use due to a low cell penetration efficiency, limitation in applicable cell types, intracellular toxicity and the like. In order to overcome these limitations, using the cell-penetrating peptides has been widely attempted in recent years.

The CPP is an oligopeptide that has properties capable of reacting with the cell membrane to cause endocytosis or directly penetrate the cell membrane, and electrochemical and physicochemical properties capable of penetrating the cell membrane.

The CPP is a part of a translocator protein, and a representative example thereof may include a membrane translocating sequence (MTS) which is a hydrophobic region present in a signal sequence of human fibroblast growth factor 4, and Tat-PTD (basic amino acid domain) of a Tat protein which is one of viral proteins of human immunodeficiency virus (HIV).

In addition, many CPPs have been reported and have been commercialized up to now. However, most of the CPPs have a low degree of transporting materials into the cell by passing through the cell membrane due to their cell-specific properties, and effects thereof are also not high. In particular, in an environment including serum or sera, the penetration efficiency of passing through the cell membrane is reduced by about half as compared to the environment without the serum. Therefore, in order to transport a functional protein, DNA, or RNA into the cell, a development of CPP that has no cell-specific properties while having a high penetration efficiency even in the presence of serum is still required.

Advantages obtained by developing a novel CPP are that various types of regulatory materials necessary for cell differentiation, cell characteristic maintenance, or function regulation of tissue and organs can be efficiently introduced into the cell. In particular, the CPP is a very useful medium that can easily migrate proteins having a very limited active period into the cell, thereby achieving the desired purpose without any expected risk. On the other hand, the CPP has advantages of being capable of transfecting the object into the cell in a recombinant form or a form mixed with the subject. Such a possibility is primarily theoretical, but has been proven in some experiments. However, as described above, due to the limitations of existing CPPs, there is still a problem entailed in the cell penetration efficiency. Briefly, due to their cell-specific properties, the existing CPPs have different migration efficiencies for the materials, and a lower delivery efficiency than other media used in gene modification. At this point, works have been actively performed to find a delivery medium that can overcome the problems entailed in the existing CPPS and have no side effect.

Therefore, it is very important to secure candidates that have excellent cell penetration efficiency and cell permeability as compared with the cell-penetrating peptides known in the art, applicability as a fusion protein, and an exclusive technical superiority over amino acid sequences thereof.

The present inventor has searched for a novel CPP in order to find a delivery medium capable of efficiently delivering various types of regulatory materials necessary for cell differentiation, cell characteristic maintenance, or function regulation of tissue and organs, and has confirmed that the problems having the conventional media can be overcome by the novel CPP, then completed the present invention based on the finding.

SUMMARY

It is an object of the present invention to provide a cell-penetrating peptide having excellent cell penetration efficiency.

In addition, another object of the present invention is to provide a recombinant cargo including the cell-penetrating peptide.

Further, another object of the present invention is to provide a cell-penetrating composition including the recombinant cargo.

Furthermore, another object of the present invention is to provide a gene construct including the cell-penetrating peptide or the recombinant cargo and an expression vector including the same.

(1) A cell-penetrating peptide including an amino acid sequence of SEQ ID NO: 1.

(2) The cell-penetrating peptide according above (1), including an amino acid sequence of SEQ ID NO: 2.

(3) The cell-penetrating peptide according above (1), including an amino acid sequence of SEQ ID NO: 3.

(4) The cell-penetrating peptide according above (1), including an amino acid sequence of SEQ ID NO: 4.

(5) A recombinant cargo including: the cell-penetrating peptide according to any one of claims 1 to 4; and a cargo which is fused at an N-terminal or C-terminal of the peptide.

(6) The recombinant cargo according above (5), wherein the cargo is a p53C peptide including an amino acid sequence of SEQ ID NO: 5.

(7) The recombinant cargo according above (6), including an amino acid sequence of SEQ ID NO: 6.

(8) The recombinant cargo according above (5), wherein the cargo is a peptide including an amino acid sequence of SEQ ID NO: 8.

(9) The recombinant cargo according above (5), including an amino acid sequence of SEQ ID NO: 9.

(10) A cell-penetrating composition including: the recombinant cargo according above (5).

(11) A recombinant expression vector including: the recombinant cargo according above (5).

The cell-penetrating peptide according to the present invention has characteristics capable of penetrating 100% into all cells within 1 hour even in an environment including serum or sera such as blood, and has a stable structure in which, even when adding a surfactant such as sodium dodecyl sulfate (SDS) thereto, the configuration is not changed. Therefore, it is possible to transport functional material into the cytoplasm or nucleoplasm, and organs in vivo while maintaining functions of the cell and the material without damaging the same, and can minimize the side effects by applying the peptide to local body parts in addition to intravascular administration.

The recombinant cargo including the cell-penetrating peptide of the present invention and a cargo fused with the peptide has a very high intracellular delivery efficiency, thus to be used to deliver various drugs by selecting various types of the cargo.

BRIEF DESCRIPTION OF THE DRAWINGS

FIG. 1 shows that the higher a value of the index than a control group (no treatment), the more peptides per unit cell can be introduced into the cell. FIG. 1 also shows that the amount of the Ara-27 peptide introduced into the cell is increased in proportion to the concentration compared with the control group or Tat-PTD.

FIG. 2 is photographs of cells taken by the fluorescence microscope after separation. Form the photographs, it could be confirmed that Tat-PTD peptides that entered in the cells were very rarely found, whereas the Ara-27 peptides that entered in the cells were found across all the cells.

As illustrated in FIG. 3, FITC fluorescence appears inside the membrane marker. Therefore, it can be seen that the peptides exist in the cell, and it can be also seen that they exist not only in the cytoplasm but also in the nucleus.

DETAILED DESCRIPTION

Figure 1:
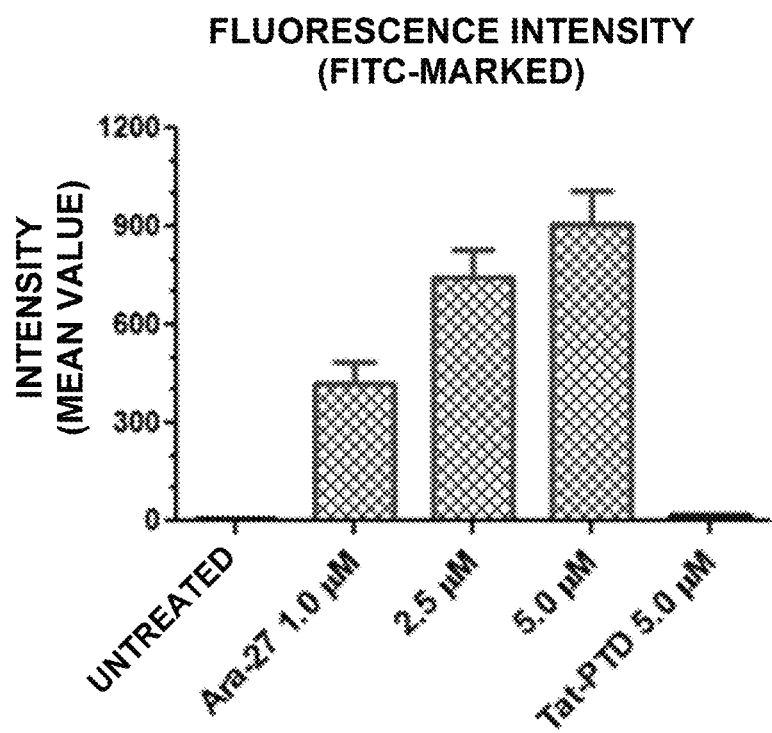
FIG. 1 is a graph showing that a cell membrane penetration efficiency of Ara-27 cell-penetrating peptide is increased in proportion to a concentration in mesenchymal stem cell (MSC) derived from a human body. In the graph, a Y axis represents a fluorescence intensity, which is an index indicating an amount of introduced peptides per unit cell.

Proteins and peptides have difficulty to penetrate the cell membrane and be delivered into the cell. Therefore, proteins and peptides have been introduced into a stem cell as a gene form and have performed a role as a cell therapy agent.

However, the present inventor has found a novel peptide that has excellent cell permeability as a peptide itself without separately being introduced into the stem cell, and the present invention has been made based on this finding.

The cell-penetrating peptide of the present invention is an *Arabidopsis thaliana*-derived peptide, and includes an amino acid sequence of SEQ ID NO: 1.

As used herein, the term "cell-penetrating peptide (CPP)" refers to a peptide capable of migrating cargos into the cell in vitro and/or in vivo.

The present inventor has separated several peptides derived from *Arabidopsis thaliana*, and confirmed that some peptides have excellent cell permeability even in an environment including serum or sera, and that these peptides commonly have the amino acid sequence of SEQ ID NO: 1. That is, it is determined that the amino acid sequence of SEQ ID NO: 1 corresponds to a part that affects the cell permeability.

Thereby, the specific sequence of the cell-penetrating peptide according to the present invention is not particularly limited, so long as it includes the amino acid sequence of SEQ ID NO: 1. The cell-penetrating peptide may include only the amino acid sequence of SEQ ID NO: 1, or may include an amino acid sequence to which some sequences are added at the N-terminus, C-terminus, or both termini thereof.

A particular example of the amino acid sequence having the sequences added thereto may include an amino acid sequence of SEQ ID NO: 2 to which some sequences are added at the N-terminus thereof, an amino acid sequence of SEQ ID NO: 3 to which some sequences are added at the N-terminus thereof, an amino acid sequence of SEQ ID NO:

4 to which some sequences are added at the N-terminus thereof, and the like, but it is not limited thereto.

In addition to the above-described sequences, the cell-penetrating peptides of the present invention may be linked to other proteins or other protein delivery domains known in the related art, and may include: for example, a trans-activating transcriptional activator (TAT) derived from human immunodeficiency virus type I (HIV-1); antennapedia (Antp) or penetratin peptide, which is antennapedia homeodomain from *Drosophila*; mutator phenotype protein 1 (Mph-1) of a mouse transcription factor; herpes simplex virus (HSV-1); viral protein 22 (VP22); human protamine P4 (HP4) from herring protamine; transportan; model amphipathic peptide (MAP); transportan-10 (TP10), cardiac targeting peptide (CTP), K5-FGF (K5-fibroblast growth factor, AAVALLPAVLLALLP (SEQ ID NO: 16)); HAP-1 (huntingtin-associated protein 1, SFHQFARATLAS (SEQ ID NO: 17)); 293P (SNNNVRPIHIWP (SEQ ID NO: 18)); CADY (cysteamidation PTD Ac-GLWRALWRLL-RSLWRLLWRA (SEQ ID NO: 19)-Cya); PF6 (PepFect6, Stearyl-AGYLLGK(cNH)INLKALAALAKKIL (SEQ ID NO: 20)-NH2); RXR (arginine rich peptide); poly-arginine (Rn (n=6 to 12)); poly-lysine, or a modified peptide thereof (e.g., a peptide in which 47 to 57 amino acid residues of a TAT protein are modified), and the like, but it is not limited thereto.

Since the cell-penetrating peptide of the present invention exhibits excellent cell permeability, it is possible to effectively deliver the cargo into the cell by linking to the cargo.

For this end, the present invention provides a recombinant cargo including the above-described cell-penetrating peptide.

The recombinant cargo of the present invention includes the above-described cell-penetrating peptide and a cargo fused to an N-terminal or C-terminal of the cell-penetrating peptide.

As used herein, the term "cargo" refers to all materials capable of linking to the cell-penetrating peptide of the present invention to be migrated into the cell. For example, the cargo may include all materials required to increase the cell penetration efficiency, specifically, materials effectively used for drugs, cosmetics or health foods, more specifically, materials which are not easily migrated into the cell through a general route, and most specifically, proteins, nucleic acids, peptides, minerals, sugar including glucose, nanoparticles, biological formulations, viruses, contrast materials, or other chemicals, but it is not limited thereto.

As used herein, the term "drug" is a broad concept that includes a material for alleviating, preventing, treating or diagnosing a disease, injury, or particular symptom. In the above embodiment, the drug delivered into the cell by the cell-penetrating peptide may further include a drug carrier such as liposome, micelle, nanoparticle, magnetic particle or quantum dot.

As used herein, the term "peptide" may include hormones, hormone analogues, enzymes, enzyme inhibitors, signal transduction proteins (or peptides), antibodies or vaccines, but it is not limited thereto. The nucleic acid may include naturally occurring or artificial DNA or RNA molecules, and may be single-stranded or double-stranded nucleic acid. The cargo may be one or more nucleic acid molecules, and may be the same type of nucleic acid molecules (e.g., having the same nucleotide sequence as each other) or other types of nucleic acid molecules. The nucleic acid may include one or more of DNA, cDNA, decoy DNA, RNA, siRNA, miRNA, shRNA, stRNA, snoRNA, snRNA, PNA, antisense oligomer, plasmid and other modified nucleic acids, but it is not limited thereto.

As used herein, the term "contrast material" refers to any material used for imaging in vivo structures or contrasting fluids during medical imaging. The contrast material may include a radiopaque contrast agent, a paramagnetic contrast agent, a superparamagnetic contrast agent, a computed tomography (CT) contrast agent, or other contrast agents, but it is not limited thereto. For example, the radiopaque contrast agent (for X-ray imaging) may include an inorganic iodine compound and an organic iodine compound (e.g., Diatrizoart), radiopaque metal and salts thereof (e.g., silver, gold, platinum, etc.), and other radiopaque compounds (e.g., calcium salts, barium salts such as barium sulphate, tantalum and tantalum oxide). The paramagnetic contrast material (for MR imaging) may include gadolinium diethylenetri-aminepentaacetic acid (Gd-DTPA) and its derivatives, and other gadolinium, manganese, iron, dysprosium, copper, europium, erbium, chromium, nickel and cobalt complexes, for example, such as 1,4,7,10-tetraazacyclododecane-N,N',N'',N'''-tetraacetic acid (DOTA), ethylenediaminetetraacetic acid (EDTA), 1,4,7,10-tetraazacyclododecane-N,-N',N''-triacetic acid (DO3A), 1,4,7-triazacyclononane-N,N',N''-triacetic acid (NOTA), 1,4,8,10-tetraazacyclotetradecane-N,N',N'',N'''-tetraacetic acid (TETA), and hydroxybenzylethylene-diamine diacetic acid (HBED). The superparamagnetic contrast agent (for MR imaging) may include magnetite, superparamagnetic iron oxide (SPIO), ultrasmall superparamagnetic iron oxide (USPIO), and monocrystalline iron oxide. Other suitable contrast agents may include iodinated and non-iodinated, ionic and non-ionic CT contrast agents, and contrast agents such as spin-labels, or other diagnostically effective agents. In addition, the contrast agent may include β-galactosidase, green fluorescent protein, blue fluorescent protein or luciferase. When expressing in the cell, the contrast agent may include a marker gene for encoding an easily detectable protein. Further, various labels such as radionuclide, fluorescent material (Fluo), enzyme, enzyme substrate, enzyme cofactor, enzyme inhibitor, and the like may be used as the contrast agent.

A particular example in which the cargo is a peptide, for example, the cargo may be an anti-cancer protein p53C including the amino acid sequence of SEQ ID NO: 5. The recombinant cargo may have an amino acid sequence in which the p53C is linked to the N-terminal or C-terminal of the above-described cell-penetrating peptide sequences. More specifically, the recombinant cargo may include the amino acid sequence of SEQ ID NO: 6 in which p53C is linked to the N-terminal of the amino acid sequence of SEQ ID NO: 4, which is referred to herein as ICT-53. In addition, ICT-53 may have a His tag adhered at the N-terminal or C-terminal for facilitating the purification. An example of a peptide to which the His tag is adhered at the N-terminal may include, for example, an amino acid sequence of SEQ ID NO: 7.

As another particular example of the case in which the cargo is the peptide, the cargo may be some sequences including an amino acid sequence of SEQ ID NO: 8 of a c-Myc protein, and the recombinant cargo may have an amino acid sequence to which the above-described some sequences are linked to the N-terminus or C-terminus of the above-described cell-penetrating peptide sequences. More specifically, the recombinant cargo may include an amino acid sequence of SEQ ID NO: 9 to which an amino acid sequence of SEQ ID NO: 8 is linked at a C-terminal of an amino acid sequence of SEQ ID NO: 4, which will be referred to herein as ICT-Myc. In addition, the ICT-Myc may have a His tag adhered to the N-terminal or C-terminal thereof for facilitating purification. An example of the peptide to which the His tag is adhered at the N-terminal may include, for example, an amino acid sequence of SEQ ID NO: 10.

In addition, the recombinant cargo of the present invention may further include a ligand, a linker, and the like that is selectively linked to a specific cell, tissue, or organ receptor so as to exhibit better specificity in vivo.

Further, the present invention may provide a cell-penetrating composition including the recombinant cargo. The cell-penetrating composition of the present invention may exhibit various effects depending on types, functions, etc. of the cargo fused to the cell-penetrating peptide. For example, when the cargo is a peptide having an anti-cancer function, the cell-penetrating composition may be used as an anti-cancer agent, and when the cargo is a peptide having a cell growth promotion function, the cell-penetrating composition may be used as a cell growth promoter. As such, effects of the peptide may vary depending on types of the cargo to be linked, such that the types of the cargo are not limited, and roles thereof are also not limited.

Furthermore, the present invention provides a gene construct that encodes the cell-penetrating peptide or recombinant cargo, and an expression vector including the same.

The cell-penetrating peptide of the present invention may be repeatedly mass produced using the gene construct and the expression vector.

In addition, when the cargo to be introduced into the cell is a protein, a polynucleotide that encodes the cargo protein is inserted into a multi-cloning site (MCS) of the expression vector including the gene construct, such that a recombinant cargo protein in which a cell membrane penetrating domain and the cargo protein are fused may be mass produced. The recombinant cargo protein produced by the expression vector may be introduced into the cell at a higher efficiency than the wild type cargo protein.

Furthermore, the present invention provides a method for delivering the cargos into the cell.

The cargo delivery method of the present invention includes the step of contacting the recombinant cargo with the cell.

Contacting between the recombinant cargo and the cell may be conducted in vitro or in vivo. When performing the contact in vitro, contacting therebetween may be executed by a process of treating the cell in a test tube with a medium containing the recombinant cargo, and culturing the same. When performing the contact in vivo, the recombinant cargo may be injected in vivo by intramuscular, intraperitoneal, intravenous, subcutaneous, intradermal, or mucosal injection, or may be administered through an oral, or nasal route, or by inhaling orally or nasally, such that the cell and the recombinant cargo come into contact with each other in vivo.

The recombinant cargo is introduced into the cell by contacting between the recombinant cargo and the cell. At the time of introducing the recombinant cargo, the higher the concentration of the recombinant cargo to be treated, the greater the amount of recombinant cargo introduced, and the longer the treated time of the recombinant cargo, the greater the amount of the recombinant cargo introduced.

The cargo delivery method of the present invention may be applied to humans or various animals other than humans without limitation thereof.

Hereinafter, preferred examples will be described to more concretely understand the present invention.

EXAMPLE (1) Synthesis of Cell-Penetrating Peptide having Greatly Higher Cell Penetration Efficiency even in an Environment including Serum or Sera And Measurement of Cell Penetration Efficiency In order to confirm the cell penetration efficiency of the cell-penetrating peptide according to the present invention, an experiment was conducted by including Tat-PTD (SEQ ID NO: 12), which is a well-known cell-penetrating peptide, as a control group.

In order to confirm the cell penetration efficiency of each cell-penetrating peptide, fluorescein isothiocyanate (FITC, fluorescent material), which fluoresces each peptide, was adhered to each peptide, then penetration efficiencies thereof were examined.

When measuring the cell penetration efficiency, in order to remove each cell-penetrating peptide which may be adhered to the cell membrane surface, a Heparin & Trypsin washing method used in the Kaplan group was applied thereto [Kaplan I M, Wadia J S, Dowdy S F (2005) Cationic TAT peptide transduction domain enters cells by macropinocytosis. J Controlled release 102: 247-253). In summary, in the experiments to be described below, each cell-penetrating peptide was put into a cell growth medium at a concentration of 1 µM, incubated for 30 minutes, and then the cells were washed 3 times with Heparin, followed by separating the cells with trypsin to perform a FACS analysis.

In the mesenchymal stem cell (MSC), an amount of the cell-penetrating peptide (Ara-27) including an amino acid sequence of SEQ ID NO: 2 into the cell was determined for each concentration.

Figure 2:
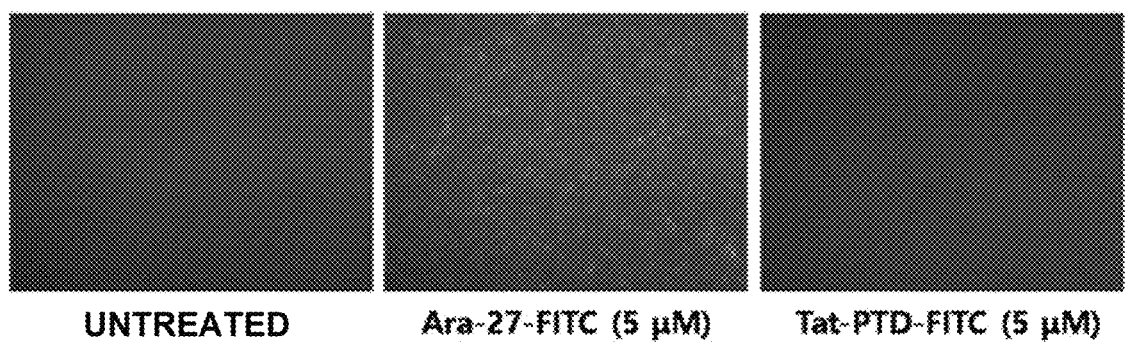
FIG. 2 shows that, in the case of the Ara-27 cell-penetrating peptide in human-derived MSCs, a large number of peptides, that can be visually confirmed by a fluorescence microscope, penetrate the cell membrane and enter the cell within 1 hour. An experiment was conducted in a medium containing 10% serum, and after treatment for 30 minutes at a concentration of 1 μM, fluorescent peptides adhered to the cell surface were removed using a heparin washing method, and then the cell was separated therefrom by treatment with trypsin.

Herein, it can be seen that the Ara-27 has characteristics that the amount of the peptide introduced per unit cell for 1 hour was increased in proportion to the concentration, but in a case of Tat-PTD, the amount of the peptide introduced per unit cell was remarkably low even at a concentration of 5 µM (FIG. 1). Also, it can be seen that the Ara-27 showed a high fluorescence intensity enough to visually confirm a strong fluorescence intensity using an optical microscope, unlike the Tat-PTD (FIG. 2).

Figure 3:
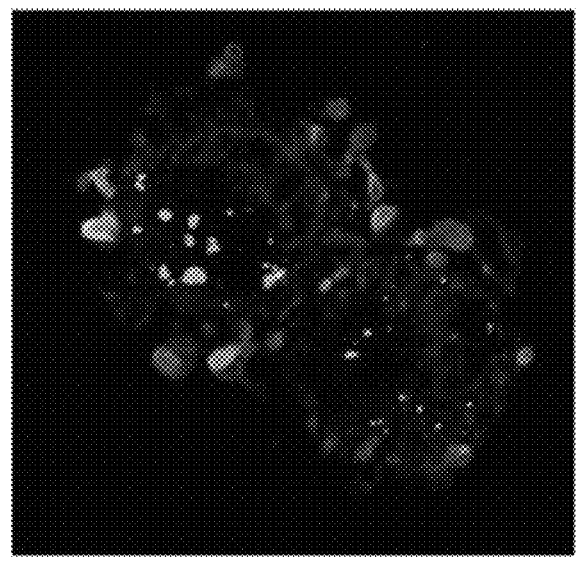
FIG. 3 is a photograph taken by a confocal microscope after 18 hours from penetration of the Ara-27 peptide (5 μM) through the cell, and shows translocation in the cell. From the photograph, it can be seen that even after one day, the peptides that penetrated the cell stably exist therein. In order to more clearly show that the peptides exist in the cell, another experiment was conducted by removing the cell adhered to the bottom using trypsin, then further treating the same with immuno-fluorescence together with a membrane marker.

Further, in order to determine whether the Ara-27 cell-penetrating peptide is actually present in intracellular nuclei or cytoplasm, the Ara-27 peptide was fluorescently treated, and then analyzed using a confocal microscope. Human mesenchymal stem cells (human MSCs) were placed in a DMEM cell culture medium containing 10% FBS in a 6-well plate. After 3 hours from the incubation, 2 µM of Ara-27 peptide was added to the medium, and then the Ara-27 peptide was treated and observed by a microscope. As a result of the observation, it can be confirmed that most of the Ara-27 peptides were present in the cytoplasm. Next, a membrane marker (FM-64) was used to examine whether the peptides are actually present inside the cell membrane. The cells were removed with trypsin to allow reagents to be inserted into the cell membrane, and the reagents were treated to perform the analysis. At this time, it can be confirmed that most of peptides were present in cytoplasmic parts inside the cell membranes, and some of the peptides were also present in the nucleus (FIG. 3).

Figure 4:
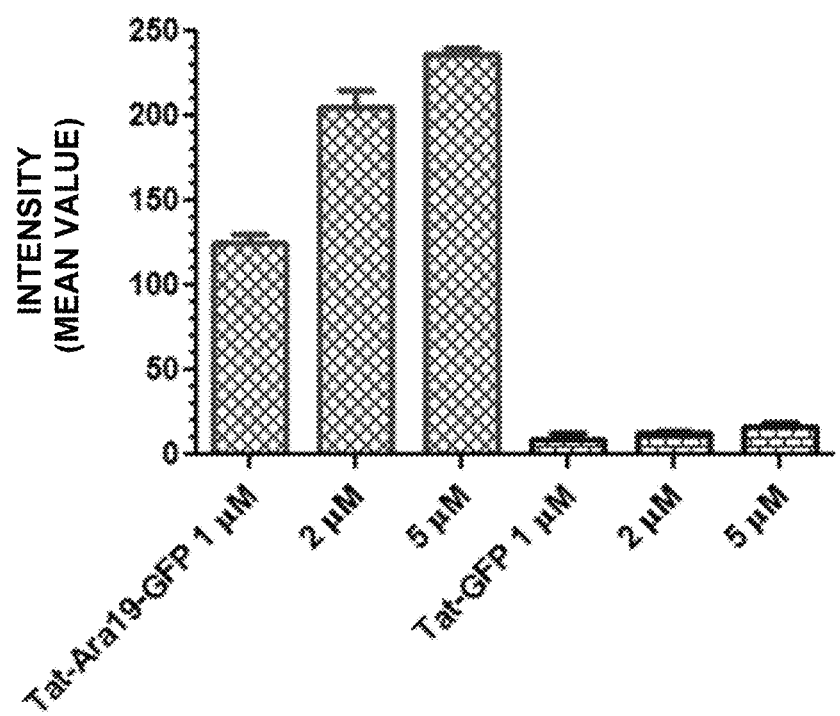
FIGS. 4 and 5 are graphs showing results of confirming migration effects of the Tat peptide (right sides in FIGS. 4 and 5) and the Tat-Ara-19 (left sides in FIGS. 4 and 5) peptide into the cell using a GFP fluorescent protein as a reporter protein.
Figure 5:
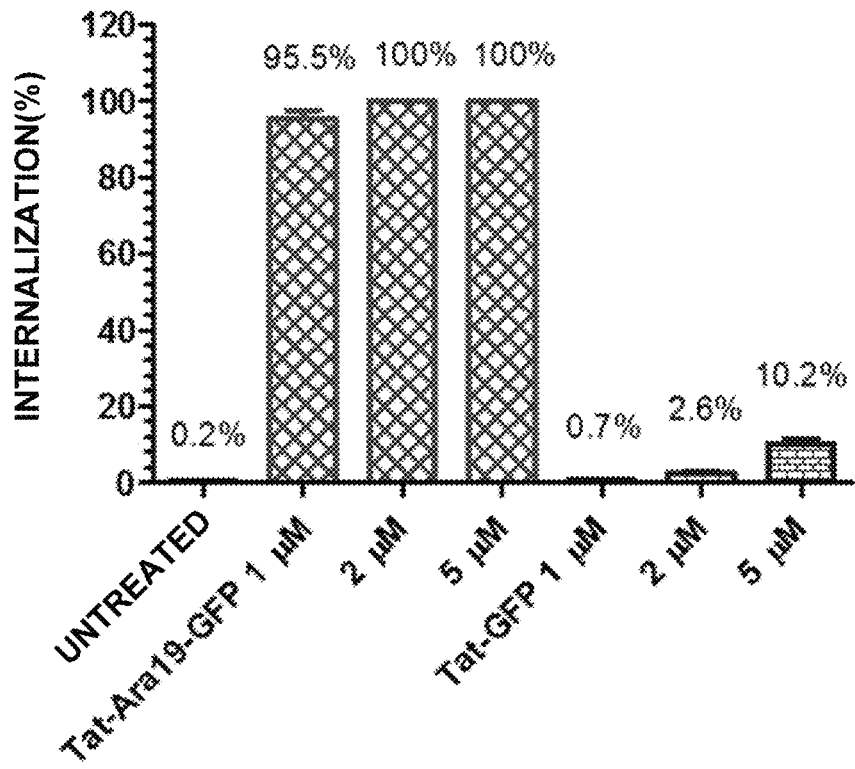
Figure 6:
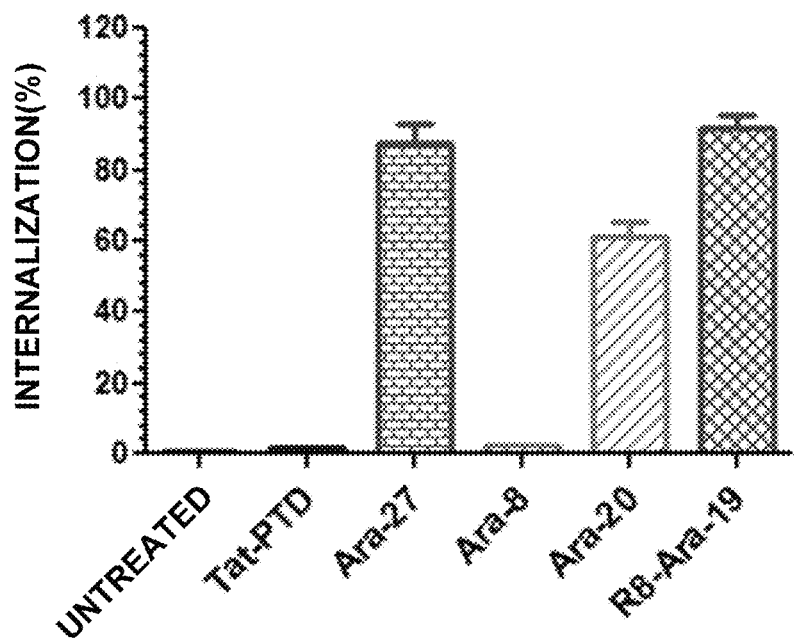
FIG. 6 is a graph showing results of comparing the cell penetration efficiencies of Ara-27, ara-20, R8-Ara-19 and Ara-8 cell-penetrating peptides in a NIH3T3 fibroblast.

In order to reconfirm whether the Ara-27 cell-penetrating peptide plays a role of inputting other materials into the cell, another experiment was conducted to examine effects of delivering the materials into the cell using a GFP fluorescent protein as a reporter protein. Then, a gene was synthesized (Tat-Ara19-GFP) (SEQ ID NO: 14) so as to be expressed in such a way that GFP (SEQ ID NO: 13) is fused to the Tat-Ara-19, and another gene was synthesized (Tat-GFP) (SEQ ID NO: 15) so as to be expressed in such a way that the GFP is fused to the Tat-PTD as a control, then expression thereof was conducted in a pET11 vector (pET-11d, Novagen Co.). Thereafter, two proteins were purified using a Ni-NTA His tag resin. Herein, skin stem cells were used to confirm cell penetrance of the two proteins. As illustrated in FIGS. 4 to 6, when fluorescently treating the two proteins for 1 hour, the Tat-GFP does not fluoresce in the cell even at a high concentration of 5 μM, whereas a state, in which the Tat-Ara 19-GFP fluoresces in the cell, was clearly observed, and brighter fluorescence intensity was exhibited at a concentration of 2 μM. This means that the number of Tat-Ara19-GFP molecules that can enter per unit cell is increased in proportion to the concentration, such that more peptides can enter the cell (FIGS. 4 and 5). Through such results, it can be considered that the Ara-27 cell-penetrating peptide may be used not only as a medium capable of reliably delivering a desired material into the cell, but also may effectively exhibit functional properties in the cell due to more molecules per unit cell being introduced into one cell over time in proportion to the concentration.

Next, the cell penetration efficiencies of Ara-27 and the cell-penetrating peptides including amino acid sequences of SEQ ID NO: 1 (Ara-20), SEQ ID NO: 3 (R8-Ara-19), and SEQ ID NO: 11 (Ara-8) of the examples in a NIH3T3 fibroblast were compared. Since the Ara-27 had 90% or more efficiency of penetrance into the cell within only 30 minutes at a concentration of 1 μM under an environment including serum, it was found that the Ara-27 is a cell-penetrating peptide having a very high cell penetration efficiency. Some peptides of the remaining cell-penetrating peptides showed higher cell membrane penetration efficiency. In contrast, the Tat-PTD exhibited a very low level of cell penetration efficiency (FIG. 6). In addition, the cell-penetrating peptides of the examples showed very high transmission efficiencies regardless of including or excluding the serum.

(2) Anti-Cancer Effect of p53C Peptide Fused with the Cell-Penetrating Peptide

It has been reported that a p53C peptide (SEQ ID NO: 5) is a peptide of a C-terminal region of a p53 protein having an anti-cancer effect, and exhibits an anti-cancer effect when performing gene expression only on the region in the cell. Based on this fact, an experiment was conducted to examine the cell permeability and anti-cancer effect for a peptide (SEQ ID NO: 6, ICT-53) in which the p53C peptide is fused to a cell-penetrating peptide including an amino acid sequence of SEQ ID NO: 4 (Tat-Ara-19).

Figure 7:
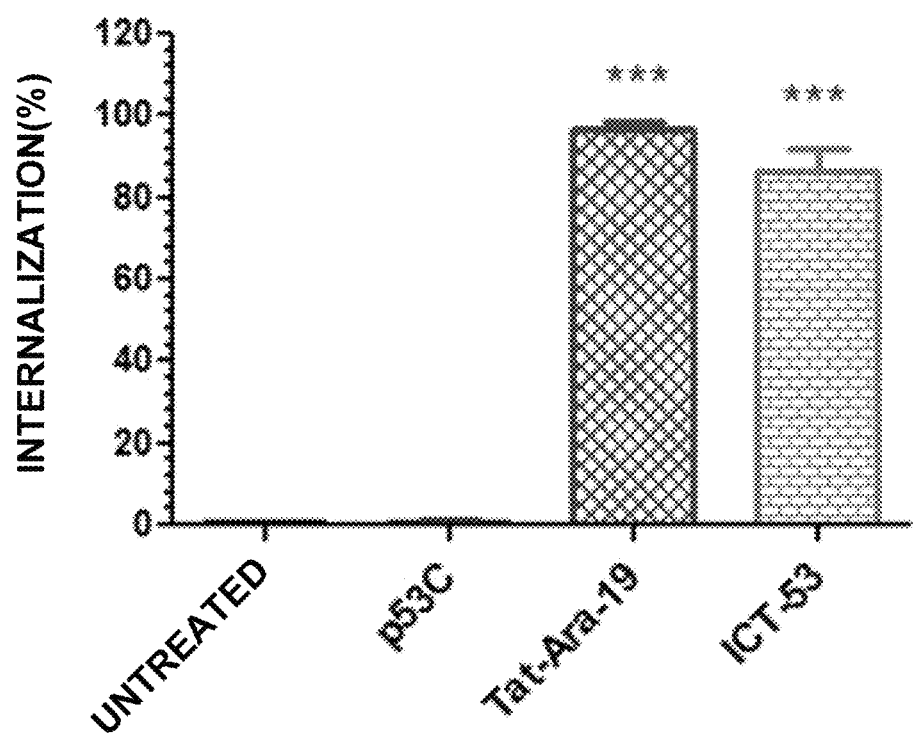
FIG. 7 is a graph showing results of comparing the cell penetration efficiencies of p53C, Tat-ara-19 and ICT-53 peptides.

A p53C peptide having 22 amino acid sequences and Tat-Ara-19 peptide, as well as the ICT-53 peptide, in which the p53C peptide is fused to the Tat-Ara-19 peptide, were synthesized, then fluorescein isothiocyanate (FITC, fluorescent material) was adhered to the C-terminus thereof so as to fluoresce. These peptides were used to examine the cell penetration efficiency for 1 hour at a concentration of 1 μM in a NIH3T3 cell line. As a result, it can be seen that the p53C peptide did not penetrate into the cell, and the Tat-Ara-19 and the ICT-53 peptides were automatically introduced into the cell with a high efficiency (FIG. 7). In this experiment, the penetration efficiency in a situation including serum was also examined.

Figure 8:
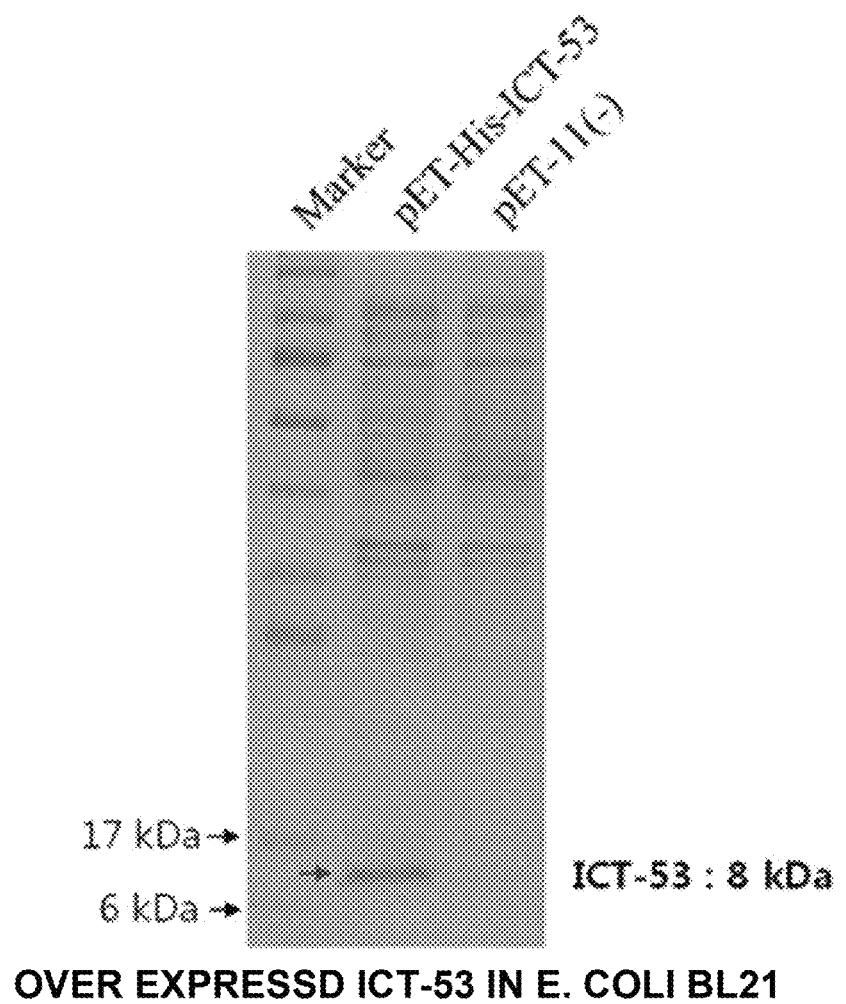
FIG. 8 is a photograph showing results of confirming that the ICT-53 peptides are stably expressed in a large amount in *E. coli*.

In order to develop a method for mass-producing a cell-penetrating anti-cancer peptide having a high cell penetration efficiency as described above in microorganisms, an expression vector was prepared by inserting a gene encoding the ICT-53 into an E. coli expression vector referred to as pET11. In order to easily purify the peptides, the expression vector was prepared so that a His tag tagged with six histidine residues and a thrombin cleavage site for separation with the His tag after the purification were input to be expressed together (SEQ ID NO: 7). In order to confirm whether the ICT-53 cell-penetrating anti-cancer peptide is expressed, E. coli strain BL21 of an expression strain was transformed to select the expression strain, followed by culturing the same. When growing to about OD 0.5, induction was performed at a concentration of 0.5 mM, and incubated at 37° C. for 6 hours. A cell wall of the E. coli expressing the ICT-53 was crushed using sonication and confirmed by sodium dodecyl sulfate polyacrylamide gel electrophoresis (SDS-PAGE). As a result, it was possible to confirm a mass expressed protein band at a position of about 8 kDa. From this result, it was confirmed by the SDS-PAGE that the ICT-53 peptides were stably mass expressed in the E. coli (FIG. 8). In addition, since the His tag is present, the peptides were purified by affinity chromatography using a Ni-NTA resin, and another experiment was further conducted to examine the anti-cancer effect of the peptide using a cancer cell line.

In order to confirm whether the purified ICT-53 peptides exhibit the anti-cancer effect, the peptides were treated in U2OS cancer cell line, which is a bone marrow cancer cell, for each concentration.

Figure 9:
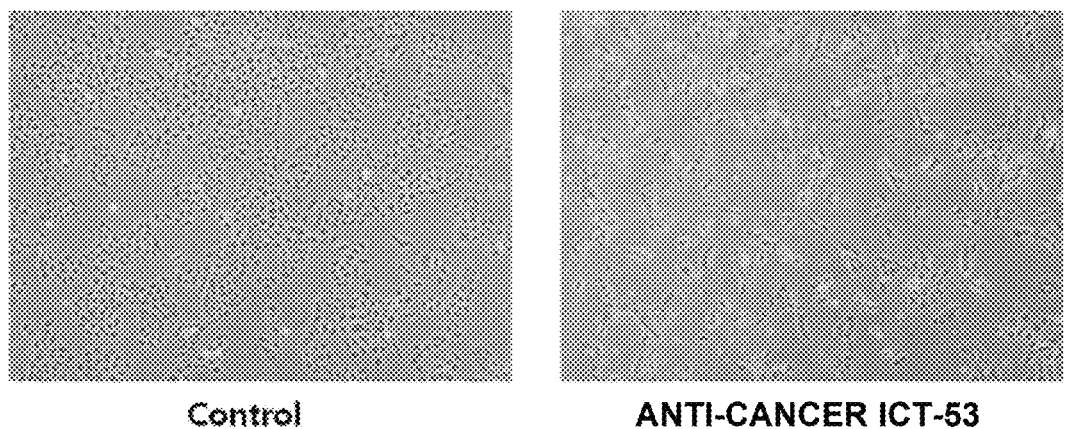
FIGS. 9 and 10 are photographs and a graph showing an anti-cancer effect of the ICT-53 peptide.
Figure 10:
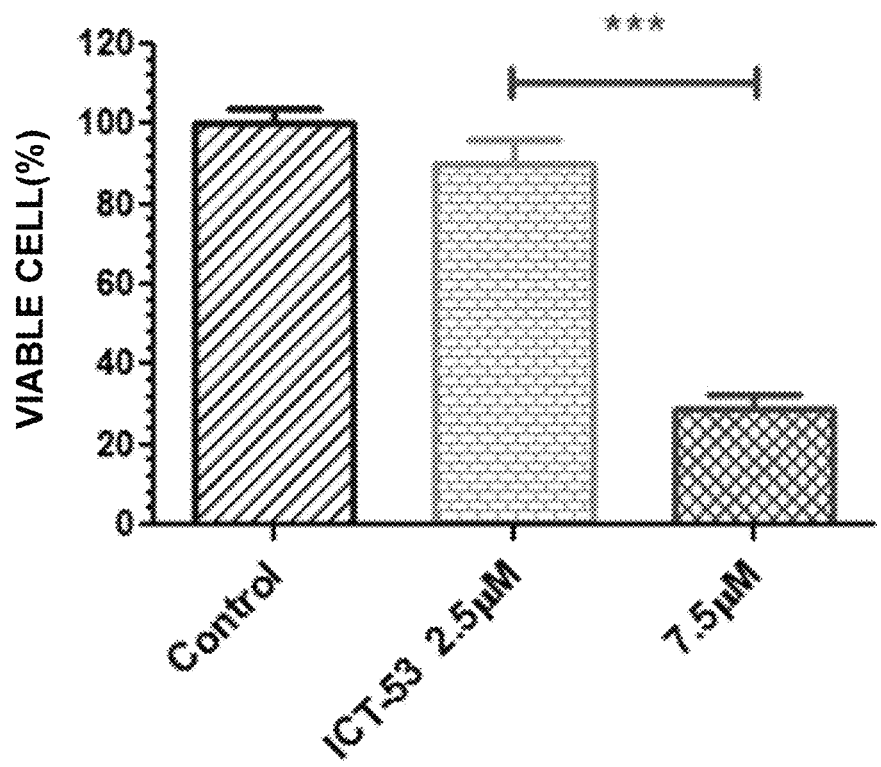

Then, it was confirmed whether the cells died in a cell group treated with an ICT-53 peptide (FIG. 9). As a result, it was confirmed that the anti-cancer effect was exhibited in proportion to the concentration even when the purified ICT-53 peptide was treated for each concentration. In particular, it was confirmed that cancer growth was inhibited about 70% by the ICT-53 peptide at a concentration of 7.5 μM (FIG. 10).

(3) Cell Growth Promotion Effect of c-Myc Peptide Fused with Ara-27 Derived Peptide p As another application example, an experiment was conducted to determine whether the cell growth promotion effect is exhibited by the cell penetration when fusing a c-Myc peptide that has an effect of promoting the cell growth with the Ara-27.

Figure 11:
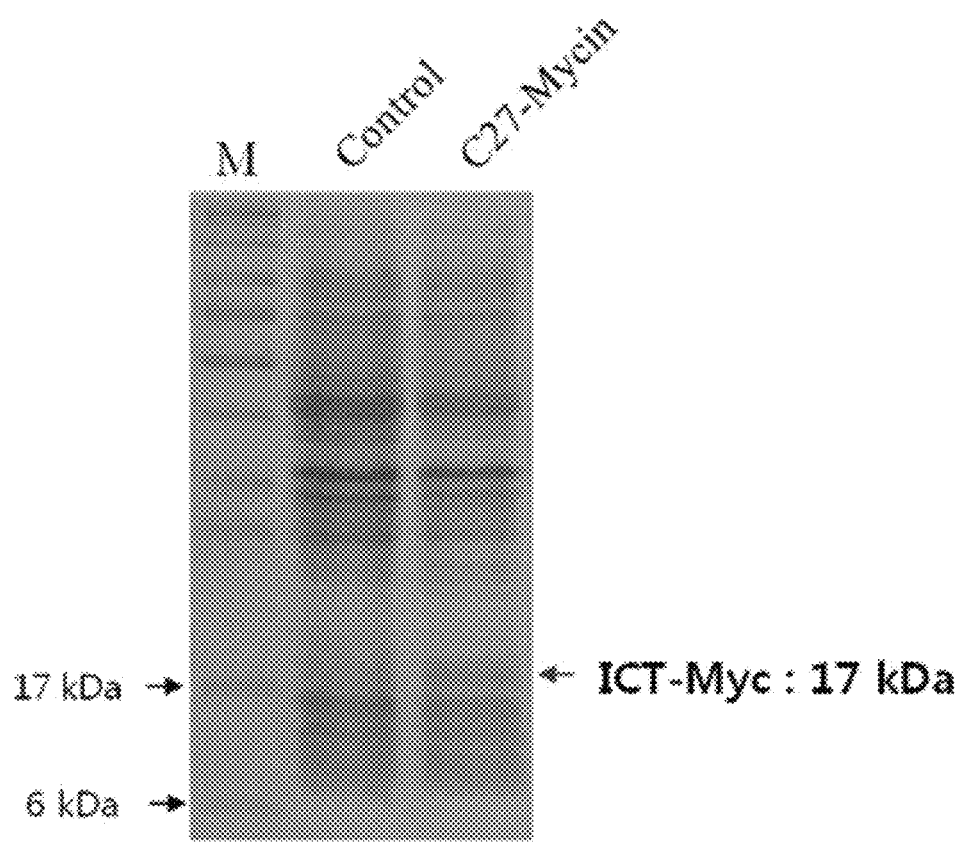
FIG. 11 is a photograph showing results of confirming that the ICT-Myc peptides are stably expressed in a large amount in *E. coli*.

In order to develop a method for mass-producing a cell-penetrating regeneration peptide having a high cell penetration efficiency in microorganisms, an expression vector was prepared by inserting a gene encoding the ICT-Myc into an E. coli expression vector referred to as pET11. In order to easily purify the peptides, the expression vector was prepared so that a His tag tagged with six histidine residues and a thrombin cleavage site for separation with the His tag after the purification were input to be expressed together (SEQ ID NO: 10). In order to confirm whether the ICT-Myc cell-penetrating regeneration peptide is expressed, E. coli strain BL21 of an expression strain was transformed to select the expression strain, followed by culturing the same. When growing to about OD 0.5, induction was performed at a concentration of 0.5 mM, and incubated at 20° C. for 18 hours. A cell wall of the E. coli expressing the ICT-Myc was crushed using sonication and confirmed by SDS-PAGE. As a result, it was possible to confirm a mass expressed protein band at a position of about 17 kDa. From this result, it was confirmed by the SDS-PAGE that the ICT-Myc peptides were stably mass expressed in the E. coli (FIG. 11). In addition, since the His tag is present, the peptides were purified by affinity chromatography using a Ni-NTA resin, and another experiment was further conducted to examine the cell growth promotion effect of the peptide using a NIH3T3 cell line.

In order to confirm that the purified ICT-Myc peptide exhibits a regeneration promotion effect, the peptides were treated in a fibroblast NIH3T3 cell line for each concentration.

Figure 12:
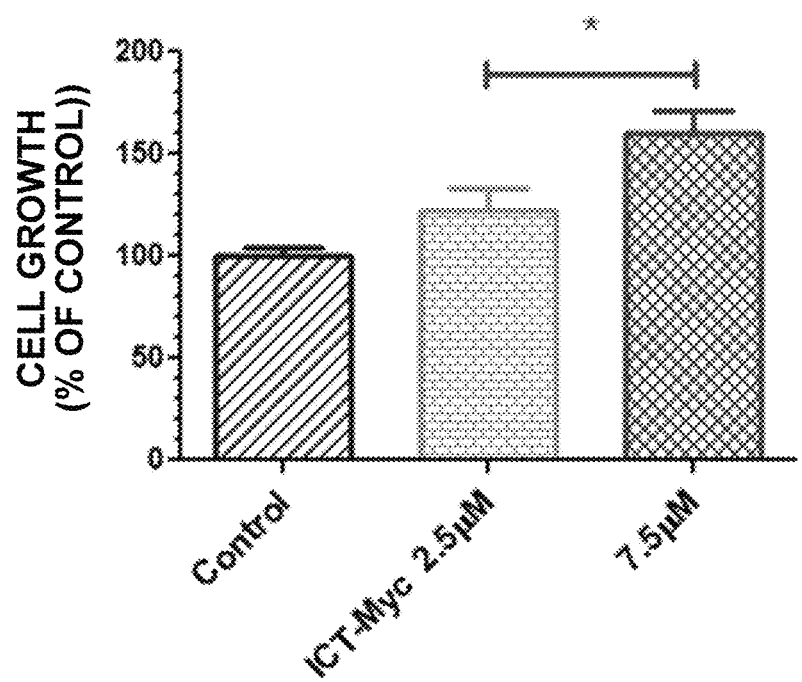
FIG. 12 is a graph showing results of confirming a growth promotion effect of the ICT-Myc peptide purified in a cell group treated with an ICT-Myc peptide.

In a cell group treated with an ICT-Myc peptide, it was found that, when the purified ICT-Myc peptide was treated for each concentration, the growth promotion effect was exhibited in proportion to the concentration. As a result, it could be confirmed that about 60% growth promotion was induced in the cells, in particular, at a concentration of 7.5 µM (FIG. 12).

The amino acid sequences disclosed in the present invention are the Ara-27 derived peptides, which are cell-penetrating peptides having high permeability into the cell, and exhibit greatly higher cell penetration efficiency than the Tat-PTD peptide. In addition, it has been found that the amino acid sequences may actually have functional properties by delivering the desired proteins, peptides or genes into the cell, in addition to the cell penetration efficiency. Therefore, it is considered that it is possible to develop not only the potential of new drug development for various materials having superior functionalities, but also other promising proteins having superior functionalities as a cell-penetrable protein.

The invention claimed is:

1. A cell-penetrating peptide comprising the amino acid sequence of SEQ ID NO: 3 or the amino acid sequence of SEQ ID NO: 4.

2. The cell-penetrating peptide of claim 1, comprising the amino acid sequence of SEQ ID NO: 4.

3. A recombinant cargo comprising:
   a cell-penetrating peptide comprising the amino acid sequence of SEQ ID NO: 1; and
   a cargo which is fused at an N-terminal or C-terminal of the peptide.

4. The recombinant cargo according to claim 3, wherein the cargo is a p53C peptide comprising the amino acid sequence of SEQ ID NO: 5.

5. The recombinant cargo according to claim 4, wherein the recombinant cargo comprises the amino acid sequence of SEQ ID NO: 6.

6. The recombinant cargo according to claim 3, wherein the cargo is a peptide comprising the amino acid sequence of SEQ ID NO: 8.

7. The recombinant cargo according to claim 3, wherein the recombinant cargo comprises the amino acid sequence of SEQ ID NO: 9.

8. A cell-penetrating composition comprising: the recombinant cargo of claim 3.

9. A recombinant expression vector comprising a polynucleotide that encodes the recombinant cargo of claim 3.

10. The cell-penetrating peptide of claim 1, comprising the amino acid sequence of SEQ ID NO: 3.

11. The recombinant cargo according to claim 3, wherein the cell-penetrating peptide comprises the amino acid sequence of SEQ ID NO: 2.

12. The recombinant cargo according to claim 3, wherein the cell-penetrating peptide comprises the amino acid sequence of SEQ ID NO: 3.

13. The recombinant cargo according to claim 3, wherein the cell-penetrating peptide comprises the amino acid sequence of SEQ ID NO: 4.

14. A cell-penetrating peptide comprising the amino acid sequence of SEQ ID NO: 1 or the amino acid sequence of SEQ ID NO: 2.

15. The cell-penetrating peptide of claim 14, wherein the cell-penetrating peptide comprises the amino acid sequence of SEQ ID NO: 1.

16. The cell-penetrating peptide of claim 14, wherein the cell-penetrating peptide comprises the amino acid sequence of SEQ ID NO: 2.

\* \* \* \* \*

SEQUENCE LISTING

```
<160> NUMBER OF SEQ ID NOS: 20

<210> SEQ ID NO 1
<211> LENGTH: 20
<212> TYPE: PRT
<213> ORGANISM: Artificial Sequence
<220> FEATURE:
<223> OTHER INFORMATION: Ara-20

<400> SEQUENCE: 1

Arg Cys Phe Arg Cys Arg Gln Ala Gly His Trp Ile Ser Asp Cys Arg
1               5                   10                  15

Leu Lys Ser Lys
            20

<210> SEQ ID NO 2
<211> LENGTH: 27
<212> TYPE: PRT
<213> ORGANISM: Artificial Sequence
<220> FEATURE:
<223> OTHER INFORMATION: Ara-27

<400> SEQUENCE: 2

Arg Asn Gln Arg Lys Thr Val Arg Cys Phe Arg Cys Arg Gln Ala Gly
1               5                   10                  15

His Trp Ile Ser Asp Cys Arg Leu Lys Ser Lys
            20                  25

<210> SEQ ID NO 3
<211> LENGTH: 27
<212> TYPE: PRT
<213> ORGANISM: Artificial Sequence
<220> FEATURE:
<223> OTHER INFORMATION: R8-Ara-19

<400> SEQUENCE: 3

Arg Arg Arg Arg Arg Arg Arg Arg Cys Phe Arg Cys Arg Gln Ala Gly
1               5                   10                  15

His Trp Ile Ser Asp Cys Arg Leu Lys Ser Lys
            20                  25

<210> SEQ ID NO 4
<211> LENGTH: 27
<212> TYPE: PRT
<213> ORGANISM: Artificial Sequence
<220> FEATURE:
<223> OTHER INFORMATION: Tat-Ara-19

<400> SEQUENCE: 4

Arg Lys Lys Arg Arg Gln Arg Arg Cys Phe Arg Cys Arg Gln Ala Gly
1               5                   10                  15
```

```
His Trp Ile Ser Asp Cys Arg Leu Lys Ser Lys
            20                  25

<210> SEQ ID NO 5
<211> LENGTH: 22
<212> TYPE: PRT
<213> ORGANISM: Artificial Sequence
<220> FEATURE:
<223> OTHER INFORMATION: p53C

<400> SEQUENCE: 5

Gly Ser Arg Ala His Ser Ser His Leu Lys Ser Lys Lys Gly Gln Ser
1               5                   10                  15

Thr Ser Arg His Lys Lys
            20

<210> SEQ ID NO 6
<211> LENGTH: 49
<212> TYPE: PRT
<213> ORGANISM: Artificial Sequence
<220> FEATURE:
<223> OTHER INFORMATION: ICT-53

<400> SEQUENCE: 6

Arg Lys Lys Arg Arg Gln Arg Arg Cys Phe Arg Cys Arg Gln Ala Gly
1               5                   10                  15

His Trp Ile Ser Asp Cys Arg Leu Lys Ser Lys Gly Ser Arg Ala His
            20                  25                  30

Ser Ser His Leu Lys Ser Lys Lys Gly Gln Ser Thr Ser Arg His Lys
        35                  40                  45

Lys

<210> SEQ ID NO 7
<211> LENGTH: 69
<212> TYPE: PRT
<213> ORGANISM: Artificial Sequence
<220> FEATURE:
<223> OTHER INFORMATION: His-ICT-53

<400> SEQUENCE: 7

Met Gly Ser Ser His His His His His His Ser Ser Gly Leu Val Pro
1               5                   10                  15

Arg Gly Ser His Arg Lys Lys Arg Arg Gln Arg Arg Cys Phe Arg Cys
            20                  25                  30

Arg Gln Ala Gly His Trp Ile Ser Asp Cys Arg Leu Lys Ser Lys Gly
        35                  40                  45

Ser Arg Ala His Ser Ser His Leu Lys Ser Lys Lys Gly Gln Ser Thr
    50                  55                  60

Ser Arg His Lys Lys
65

<210> SEQ ID NO 8
<211> LENGTH: 86
<212> TYPE: PRT
<213> ORGANISM: Artificial Sequence
<220> FEATURE:
<223> OTHER INFORMATION: Part of c-Myc

<400> SEQUENCE: 8

Val Lys Arg Arg Thr His Asn Val Leu Glu Arg Gln Arg Arg Asn Glu
1               5                   10                  15
```

```
Leu Lys Arg Ser Phe Phe Ala Leu Arg Asp Gln Ile Pro Glu Leu Glu
             20                  25                  30

Asn Asn Glu Lys Ala Pro Lys Val Val Ile Leu Lys Lys Ala Thr Ala
             35                  40                  45

Tyr Ile Leu Ser Val Gln Ala Glu Glu Gln Lys Leu Ile Ser Glu Glu
 50                  55                  60

Asp Leu Leu Arg Lys Arg Arg Glu Gln Leu Lys His Lys Leu Glu Gln
 65                  70                  75                  80

Leu Arg Asn Ser Cys Ala
                 85

<210> SEQ ID NO 9
<211> LENGTH: 113
<212> TYPE: PRT
<213> ORGANISM: Artificial Sequence
<220> FEATURE:
<223> OTHER INFORMATION: ICT-Myc

<400> SEQUENCE: 9

Arg Lys Lys Arg Arg Gln Arg Arg Cys Phe Arg Cys Arg Gln Ala Gly
 1               5                   10                  15

His Trp Ile Ser Asp Cys Arg Leu Lys Ser Lys Val Lys Arg Arg Thr
             20                  25                  30

His Asn Val Leu Glu Arg Gln Arg Arg Asn Glu Leu Lys Arg Ser Phe
             35                  40                  45

Phe Ala Leu Arg Asp Gln Ile Pro Glu Leu Glu Asn Asn Glu Lys Ala
 50                  55                  60

Pro Lys Val Val Ile Leu Lys Lys Ala Thr Ala Tyr Ile Leu Ser Val
 65                  70                  75                  80

Gln Ala Glu Glu Gln Lys Leu Ile Ser Glu Glu Asp Leu Leu Arg Lys
                 85                  90                  95

Arg Arg Glu Gln Leu Lys His Lys Leu Glu Gln Leu Arg Asn Ser Cys
                100                 105                 110

Ala

<210> SEQ ID NO 10
<211> LENGTH: 133
<212> TYPE: PRT
<213> ORGANISM: Artificial Sequence
<220> FEATURE:
<223> OTHER INFORMATION: His-ICT-Myc

<400> SEQUENCE: 10

Met Gly Ser Ser His His His His Ser Ser Gly Leu Val Pro
 1               5                   10                  15

Arg Gly Ser His Arg Lys Lys Arg Arg Gln Arg Arg Cys Phe Arg Cys
             20                  25                  30

Arg Gln Ala Gly His Trp Ile Ser Asp Cys Arg Leu Lys Ser Lys Val
             35                  40                  45

Lys Arg Arg Thr His Asn Val Leu Glu Arg Gln Arg Arg Asn Glu Leu
 50                  55                  60

Lys Arg Ser Phe Phe Ala Leu Arg Asp Gln Ile Pro Glu Leu Glu Asn
 65                  70                  75                  80

Asn Glu Lys Ala Pro Lys Val Val Ile Leu Lys Lys Ala Thr Ala Tyr
                 85                  90                  95

Ile Leu Ser Val Gln Ala Glu Glu Gln Lys Leu Ile Ser Glu Glu Asp
                100                 105                 110
```

Leu Leu Arg Lys Arg Arg Glu Gln Leu Lys His Lys Leu Glu Gln Leu
        115                 120                 125

Arg Asn Ser Cys Ala
    130

<210> SEQ ID NO 11
<211> LENGTH: 8
<212> TYPE: PRT
<213> ORGANISM: Arabidopsis thaliana

<400> SEQUENCE: 11

Arg Asn Gln Arg Lys Thr Val Arg
1               5

<210> SEQ ID NO 12
<211> LENGTH: 8
<212> TYPE: PRT
<213> ORGANISM: Artificial Sequence
<220> FEATURE:
<223> OTHER INFORMATION: Tat-PTD

<400> SEQUENCE: 12

Arg Lys Lys Arg Arg Gln Arg Arg
1               5

<210> SEQ ID NO 13
<211> LENGTH: 759
<212> TYPE: DNA
<213> ORGANISM: Artificial Sequence
<220> FEATURE:
<223> OTHER INFORMATION: GFP derived from pEGFP-1(Clontech)

<400> SEQUENCE: 13
atggtgagca agggcgagga gctgttcacc ggggtggtgc ccatcctggt cgagctgggc      60
ggcgacgtaa acggccacaa gttcagcgtg tccggcgagg gcgagggcga tgccacctac     120
ggcaagctga ccctgaagtt catctgcacc accggcaagc tgcccgtgcc ctggcccacc     180
ctcgtgacca ccctgaccta cggcgtgcag tgcttcagcc gctaccccga ccacatgaag     240
cagcacgact tcttcaagtc cgccatgccc gaaggctacg tccaggagcg caccatcttc     300
ttcaaggacg acggcaacta caagacccgc gccgaggtga agttcgaggg cgacaccctg     360
gtgaaccgca tcgagctgaa gggcatcgac ttcaaggagg acggcaacat cctggggcac     420
aagctggagt acaactacaa cagccacaac gtctatatca tggccgacaa gcagaagaac     480
ggcatcaagg tgaacttcaa gatccgccac aacatcgagg acggcagcgt gcagctcgcc     540
gaccactacc agcagaacac ccccatcggc gacggccccg tgctgctgcc cgacaaccac     600
tacctgagca cccagtccgc cctgagcaaa gaccccaacg agaagcgcga tcacatggtc     660
ctgctggagt tcgtgaccgc cgccgggatc actctcggca tggacgagct gtacaagaag     720
cttgcggccg cactcgagca ccaccaccac caccactga                             759

<210> SEQ ID NO 14
<211> LENGTH: 855
<212> TYPE: DNA
<213> ORGANISM: Artificial Sequence
<220> FEATURE:
<223> OTHER INFORMATION: Tat-Ara19-GFP

<400> SEQUENCE: 14
catatgcgta aaaaacgtcg ccagcgtcgc tgctttcgtt gccgtcaggc gggccattgg      60
attagcgatt gccgtctgaa agcaaaatta ccggaatggt gagcaagggc gaggagctg     120

```
ttcaccgggg tggtgcccat cctggtcgag ctgggcggcg acgtaaacgg ccacaagttc      180
agcgtgtccg gcgagggcga gggcgatgcc acctacggca agctgaccct gaagttcatc      240
tgcaccaccg gcaagctgcc cgtgccctgg cccaccctcg tgaccaccct gacctacggc      300
gtgcagtgct tcagccgcta ccccgaccac atgaagcagc acgacttctt caagtccgcc      360
atgcccgaag gctacgtcca ggagcgcacc atcttcttca aggacgacgg caactacaag      420
acccgcgccg aggtgaagtt cgagggcgac accctggtga accgcatcga gctgaagggc      480
atcgacttca aggaggacgg caacatcctg ggcacaagc tggagtacaa ctacaacagc       540
cacaacgtct atatcatggc cgacaagcag aagaacggca tcaaggtgaa cttcaagatc      600
cgccacaaca tcgaggacgg cagcgtgcag ctcgccgacc actaccagca gaacacccc       660 atcggcgacg gccccgtgct gctgcccgac aaccactacc tgagcaccca gtccgccctg      720
agcaaagacc ccaacgagaa gcgcgatcac atggtcctgc tggagttcgt gaccgccgcc      780
gggatcactc tcggcatgga cgagctgtac aagaagcttg cggccgcact cgagcaccac      840
caccaccacc actga                                                      855
```

```
<210> SEQ ID NO 15
<211> LENGTH: 798
<212> TYPE: DNA
<213> ORGANISM: Artificial Sequence
<220> FEATURE:
<223> OTHER INFORMATION: Tat-GFP

<400> SEQUENCE: 15
catatgcgta aaaacgtcg ccagcgtcgc ttatccggaa tggtgagcaa gggcgaggag        60
ctgttcaccg gggtggtgcc catcctggtc gagctgggcg cgacgtaaa cggccacaag       120 ttcagcgtgt ccggcgaggg cgagggcgat gccacctacg gcaagctgac cctgaagttc      180
atctgcacca ccggcaagct gcccgtgccc tggcccaccc tcgtgaccac cctgacctac      240
ggcgtgcagt gcttcagccg ctaccccgac cacatgaagc agcacgactt cttcaagtcc      300
gccatgcccg aaggctacgt ccaggagcgc accatcttct tcaaggacga cggcaactac      360
aagacccgcg ccgaggtgaa gttcgagggc gacaccctgg tgaaccgcat cgagctgaag      420
ggcatcgact tcaaggagga cggcaacatc ctgggcaca agctggagta caactacaac       480
agccacaacg tctatatcat ggccgacaag cagaagaacg gcatcaaggt gaacttcaag      540
atccgccaca catcgagga cggcagcgtg cagctcgccg accactacca gcagaacacc       600
cccatcggca cgccccgt gctgctgccc gacaaccact acctgagcac ccagtccgcc        660
ctgagcaaag accccaacga gaagcgcgat cacatggtcc tgctggagtt cgtgaccgcc      720
gccgggatca ctctcggcat ggacgagctg tacaagaagc ttgcggccgc actcgagcac      780
caccaccacc accactga                                                   798
```

```
<210> SEQ ID NO 16
<211> LENGTH: 15
<212> TYPE: PRT
<213> ORGANISM: Artificial Sequence
<220> FEATURE:
<223> OTHER INFORMATION: K5-fibroblast growth factor

<400> SEQUENCE: 16

Ala Ala Val Ala Leu Leu Pro Ala Val Leu Leu Ala Leu Leu Pro
1               5                   10                  15
```

```
<210> SEQ ID NO 17
<211> LENGTH: 12
<212> TYPE: PRT
<213> ORGANISM: Artificial Sequence
<220> FEATURE:
<223> OTHER INFORMATION: huntingtin-associated protein 1

<400> SEQUENCE: 17

Ser Phe His Gln Phe Ala Arg Ala Thr Leu Ala Ser
1               5                   10

<210> SEQ ID NO 18
<211> LENGTH: 12
<212> TYPE: PRT
<213> ORGANISM: Artificial Sequence
<220> FEATURE:
<223> OTHER INFORMATION: 293P

<400> SEQUENCE: 18

Ser Asn Asn Asn Val Arg Pro Ile His Ile Trp Pro
1               5                   10

<210> SEQ ID NO 19
<211> LENGTH: 20
<212> TYPE: PRT
<213> ORGANISM: Artificial Sequence
<220> FEATURE:
<223> OTHER INFORMATION: cysteamidation

<400> SEQUENCE: 19

Gly Leu Trp Arg Ala Leu Trp Arg Leu Leu Arg Ser Leu Trp Arg Leu
1               5                   10                  15

Leu Trp Arg Ala
            20

<210> SEQ ID NO 20
<211> LENGTH: 14
<212> TYPE: PRT
<213> ORGANISM: Artificial Sequence
<220> FEATURE:
<223> OTHER INFORMATION: PepFect6

<400> SEQUENCE: 20

Ile Asn Leu Lys Ala Leu Ala Ala Leu Ala Lys Lys Ile Leu
1               5                   10
```